United States Patent [19]

Thorpe et al.

[11] 4,301,283

[45] Nov. 17, 1981

[54] PROCESS FOR PREPARING 2-OXO-DIHYDROBENZO(D)(1,3)-OXAZINES

[75] Inventors: John G. Thorpe; Peter G. Urben, both of Gosforth, England

[73] Assignee: Sterling Drug Inc., New York, N.Y.

[21] Appl. No.: 185,990

[22] Filed: Sep. 10, 1980

[30] Foreign Application Priority Data

Sep. 27, 1979 [GB] United Kingdom ............... 33442/79

[51] Int. Cl.³ ........................................... C07D 265/18
[52] U.S. Cl. ........................................................ 544/92
[58] Field of Search .......................................... 544/92

[56] References Cited

U.S. PATENT DOCUMENTS 3,705,154  12/1972  Aelony et al. .................. 260/244 R

OTHER PUBLICATIONS

Graebe et al., *Chem. Ber.* vol. 35, pp. 2751–2752 (1902).

Lindemann et al., *Ann. Chem.*, vol. 464, pp. 245–247 (1928).
Starks., *J. Amer. Chem. Soc.*, vol. 93, p. 195 (1971).
Dehmlow, *Angew. Chem.*, Int. Ed. vol. 13, p. 170 (1974).
Lee et al., *Tetrahedron Letters*, No. 20, pp. 1641–1644 (1976).

*Primary Examiner*—John M. Ford
*Attorney, Agent, or Firm*—Frederik W. Stonner; B. Woodrow Wyatt

[57] ABSTRACT

A process for preparing 2-oxo-dihydrobenzo[d][1,3]oxazines (also named 1,4-dihydro-2H-3,1-benzoxazin-2-ones) which process comprises treating a suspension or solution of a 2-carbamoyl-benzyl alcohol in a substantially water-immiscible organic medium with aqueous alkaline hypochlorite or hypobromite having a pH of at least 11 in the presence of a phase transfer catalyst; and conversion of the 2-oxo-dihydrobenzo[d][1,3]oxazines to corresponding 2-amino-benzyl alcohols which are useful as intermediates in the production of dyes, pharmaceuticals and herbicides.

31 Claims, No Drawings

PROCESS FOR PREPARING 2-OXO-DIHYDROBENZO(D)(1,3)-OXAZINES

BACKGROUND OF THE INVENTION

1. Field of the Invention

The invention relates to a process for preparing 2-oxo-dihydrobenzo[d][1,3]-oxazines (also named 1,4-dihydro-2H-3,1-benzoxazin-2-ones) and to the conversion of those products to the corresponding 2-amino-benzyl alcohols which are useful as intermediates in the production of pharmaceuticals, herbicides and dyestuffs.

2. Description of the Prior Art

In chemical synthesis, when it is desired to prepare an aniline, it is usual to employ one of two general approaches, one being the Hofmann rearrangement of benzamides, and the other being the hydrogenation of nitrobenzenes. However both of these approaches run into great difficulties when applied to the preparation of 2-amino-benzyl alcohols, either the unsubstituted compound or a substituted derivative thereof, due to side reactions involving the reactive —$CH_2OH$ group. In the case of a Hofmann rearrangement, internal nucleophilic attack by the —$CH_2OH$ group may result in the formation of a phthalide, or oxidation of the —$CH_2OH$ group may result in benzaldehydes and benzoic acids. In a hydrogenation reaction the —$CH_2OH$ group may be hydrogenated to a methyl group.

As far as is known, the only 2-amino-benzyl alcohol in commercial production is 2-amino-benzyl alcohol itself, and neither of the above approaches has been used in its preparation. It has previously been found necessary to resort to the reduction of anthranilic acid using lithium aluminum hydride, but lithium aluminum hydride is an expensive reagent and is notoriously difficult to handle on any scale, particularly because of its tendency to cause fires.

Graebe et al. Chem. Ber. 35, 2751–52 (1902) describes the conversion of salicylamide by alkaline hypochlorite to 4,5-benzoxazolone.

Lindemann et al. Ann. Chem. 464, 245–7 (1928) describes the conversion of 2-hydroxymethyl-2-benzoylazide in refluxing benzene to 2-oxo-dihydrobenzo[d][1,3]oxazine and hydrolysis of the latter with sodium hydroxide to 2-aminobenzyl alcohol.

Aelony et al. U.S. Pat. No. 3,705,154 describes the thermolytic conversion of trimethylammonium-N-(2-hydroxymethylbenzoyl)-imine to 2-oxo-dihydrobenzo[d][1,3]oxazine.

Starks J. Amer. Chem. Soc. 93, 195 (1971) and Dehmlow Angew. Chem., Int. Ed. English 13, 170 (1974) describe the use of quaternary ammonium and phosphonium salts as phase transfer catalysts in two-phase reactions.

Lee et al. Tetrahedron Lett. 1976, 1641–44 describes the phase transfer catalyzed oxidations of alcohols and amines by aqueous hypochlorite.

SUMMARY OF THE INVENTION

It has now been discovered that when 2-carbamoyl-benzyl alcohols are subjected to a Hofmann-type rearrangement performed under specific reaction conditions, there are obtained 2-oxo-dihydrobenzo[d][1,3]oxazines which are stable internal carbamic acid esters. The 2-oxo-dihydrobenzo[d][1,3]oxazines can be converted by hydrolysis to the corresponding 2-amino-benzyl alcohols.

Thus, in one aspect of the invention there is provided a process for preparing a 2-oxo-dihydrobenzo[d][1,3]oxazine of the general formula:

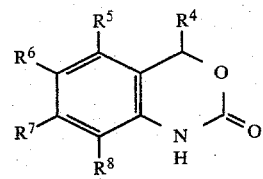

I wherein $R^4$ represents hydrogen or a substituent selected from the group consisting of alkyl of 1 to 6 carbon atoms, phenyl and phenyl substituted by a substituent selected from the group consisting of alkyl of 1 to 4 carbon atoms, alkoxy of 1 to 4 carbon atoms, halo and nitro; $R^5$ and $R^8$, which can be the same or different, each represents hydrogen or a substituent selected from the group consisting of alkyl of 1 to 3 carbon atoms, alkoxy of 1 to 3 carbon atoms and halo; and $R^6$ and $R^7$, which can be the same or different, each represents hydrogen or a substituent selected from the group consisting of alkyl of 1 to 3 carbon atoms, alkoxy of 1 to 3 carbon atoms, halo and nitro; with the proviso that at least two of $R^5$, $R^6$, $R^7$ and $R^8$ are hydrogen, which comprises suspending or dissolving in a substantially water-immiscible organic medium a 2-carbamoyl-benzyl alcohol of the general formula:

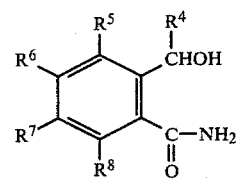

II wherein $R^4$, $R^5$, $R^6$, $R^7$ and $R^8$ are as defined above and treating the formed solution or suspension with an aqueous alkaline solution of a hypochlorite and/or hypobromite having a pH of at least 11 in the presence of a phase transfer catalyst to obtain the compound of general formula I.

In another aspect of the invention there is provided a process for preparing a 2-amino-benzyl alcohol of the general formula:

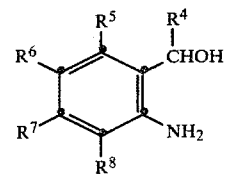

III wherein $R^4$, $R^5$, $R^6$, $R^7$ and $R^8$ are as defined hereinabove for formula I which comprises preparing a 2-oxo-dihydrobenzo[d][1,3]oxazine of formula I by the process defined hereinabove and hydrolyzing the so obtained 2-oxo-dihydrobenzo[d][1,3]-oxazine of formula I to obtain the compound of formula III.

The 2-amino-benzyl alcohols of formula III have utility as intermediates in the production of dyes, herbicides and pharmaceuticals, for example, see U.S. Pat.

No. 3,711,476, No. 3,763,158, No. 3,910,917, No. 3,914,421, No. 3,917,592, No. 3,932,407 and No. 3,950,393.

DETAILED DESCRIPTION INCLUSIVE OF THE PREFERRED EMBODIMENTS

The term alkyl as used herein refers to straight and branched alkyl.

The term halo as used herein refers to bromo, chloro, fluoro and iodo.

When $R_4$ is substituted phenyl, the substituent can occur at position 2, 3 or 4 of phenyl.

Where in discussing the process of the invention quantities are defined herein in molar terms, those molar quantities are based on the amount of 2-carbamoyl-benzyl alcohol starting material employed.

By employing suitable starting materials of general formula II in which at least one of $R^4$, $R^5$, $R^6$, $R^7$ and $R^8$ does not represent hydrogen, substituted 2-oxo-dihydrobenzo[d][1,3]oxazines may be prepared. For example, 6-nitro-2-oxo-dihydrobenzo[d][1,3]oxazines may be prepared from a compound of general formula II wherein $R^4$, $R^5$, $R^7$ and $R^8$ represent hydrogen atoms and $R^6$ represents a nitro group. However, this invention particularly concerns the preparation of unsubstituted 2-oxo-dihydrobenzo[d][1,3]oxazine, that is, a compound of general formula I wherein $R^4$, $R^5$, $R^6$, $R^7$ and $R^8$ each represent hydrogen.

A wide range of substantially water immiscible organic media may be employed to dissolve or suspend the 2-carbamoyl-benzyl alcohol of general formula II. The qualification "substantially water immiscible" means that the organic medium chosen must form a stable two-phase system with the alkaline solution of hypochlorite or hypobromite. Such media need not be totally water-immiscible, indeed virtually all so-called "water immiscible" organic liquids are capable of mixing with water, albeit to a small degree. Both aromatic and aliphatic organic liquids may be used as the organic medium, at present aromatic hydrocarbons, chlorinated hydrocarbons and esters are preferred. Particularly good results have been obtained with alkyl-substituted arenes and carboxylic acid esters. The medium at present preferred above all other is isopropyl acetate.

It is preferred in practice for the hypobromite or hypochlorite to be employed at a rate of 0.95 to 1.3 moles, and very preferably in substantially equimolar quantities. If greater amounts of hypobromite or hypochlorite are used the yield of the desired carbamic acid internal ester of general formula I tends to decrease. If less than 0.95 mole of hypobromite or hypochlorite is employed, then there is a significant amount of carbamoyl benzyl alcohol starting material left unreacted.

Hypochlorite is generally preferred as it is cheaper and more readily available. The hypochlorite may be an alkaline-earth metal salt, but alkali-metal hypochlorites are preferred. Such hypochlorites are readily available as aqueous solutions which generally contain up to 16% available chlorine. It is possible to use solutions containing 6% available chlorine or less, but it is advantageous to use more concentrated solutions since these occupy less space in the reaction vessel.

The hypochlorite is most conveniently employed as the sodium salt.

The hypochlorite or hypobromite may be prepared immediately before use by introducing chlorine or bromine, as appropriate, into an aqueous alkali-metal hydroxide solution. The introduction of chlorine to form a hypochlorite should desirably be effected with the aqueous alkali-metal hydroxide cooled in an ice-bath.

In any event, the aqueous solution of hypochlorite or hypobromite must be alkaline and have a pH of 11 or higher (more alkaline). At a lower (more acidic) pH, the yield of the desired product is drastically reduced, and there is a tendency for hydroxymethyl-benzoate salts to be formed with the evolution of nitrogen. To maximize yields of the desired 2-oxo-dihydrobenzo[d][1,3]oxazine, the pH is preferably at least 11.5. Because of the practical difficulty of measuring pH in a very alkaline environment it is difficult to define optimum conditions of alkalinity in terms of pH, but it is believed that a pH of 12 or greater provides excellent yields of the desired product.

To achieve the desired pH an appropriate base may be added to the solution of hypochlorite or hypobromite. A strong base is needed, and by way of illustration, it may be said that strong bases that may be used are those which form aqueous solutions having a pH greater than 11.5; the pH of such aqueous solutions is only to a limited extent dependent on concentration, so that it is believed that this illustration provides sufficient information to enable a suitable base to be chosen. Alkali-metal hydroxides are particularly suitable bases, but it is also possible to employ alkaline-earth metal hydroxides and basic phosphates such as trisodium phosphate. Carbonates are, however, not suitable bases. The preferred base is sodium hydroxide.

When using sodium hydroxide it has been found advantageous to employ from 3 to 30 mole % of the base. Thus, in particular when using substantially equimolar quantities of hypobromite or hypochlorite there may preferably be used about 2% w/w sodium hydroxide based on the weight of hypochlorite or hypobromite salt.

The process of the invention is carried out in the presence of a phase transfer catalyst or PTC. Such catalysts are well-known, being compounds which are capable of forming with a reactive anion an organic soluble ion pair which may then transport the reactive anion between organic and aqueous phases. Such catalysts are generally, but not exclusively, used to transport anions from an aqueous phase to an organic phase, and such is believed to be the case in the present invention.

At present there are three main classes of PTC that are used in synthesis:

(1) quaternary ammonium salts, and particularly those having from 8 to 40 carbon atoms ($C_8$–$C_{40}$);
(2) tetra-alkyl phosphonium salts, again particularly $C_8$–$C_{40}$ phosphonium salts; and
(3) polyethers, including polyethylene glycols and particularly;
 (a) crown ethers, and
 (b) cryptates (bicyclic ethers)

Of these catalysts the quaternary ammonium salts are especially preferred for use in the process of this invention. The halides such as the chlorides or bromides are the salts which are most conveniently employed, and examples of particular salts are tetrabutyl ammonium bromide, methyl trioctyl ammonium chloride, benzyl triethylammonium chloride and benzyl triethylammonium bromide. It has been found that $C_{10}$–$C_{30}$ quaternary ammonium salts are most preferably used as the PTC in this invention. Examples of commercially available quaternary ammonium salts are Adogen 464 (containing methyl trioctyl ammonium chloride and available from Ashland Chemical Company) and the similar Aliquat 336 (available from General Mills Chemical Inc.).

The amount of the catalyst is not critical, and is to an extent determined by the particular PTC selected. By way of illustration the catalyst may generally be employed in an amount of from 0.1 mole % to 5 mole %, and typically at 1 mole %.

It is preferred for the catalyst to be dissolved in the organic medium before treatment with the aqueous alkaline solution of hypobromite or hypochlorite.

The two phase system containing the reactants and the PTC should be mixed to promote the desired reaction to form the product of general formula I, and such mixing is commonplace in reactions carried out in a plurality of phases. The method of mixing is not crucial, but is obviously desirable for it to be as comprehensive as possible. Preferably all phases present should be so dispersed as to be macroscopically homogeneous and also turbulent throughout. However, acceptable yields will still result with partial stratification, or if bulk turbulence is limited to the region to which the hypobromite or hypochlorite is charged, with slower mixing around its edges.

It has been found that the process of the invention is also catalyzed by bromide ions, which may either be introduced as part of the PTC or as a separate bromide salt. Metal bromides may be used to introduce bromide ions, and alkali-metal bromides such as potassium bromide are particularly preferred. The bromide ions are very preferably present in an amount substantially equimolar with the PTC. If lesser amounts of bromide ions are employed the catalytic effect is reduced, while the presence of larger amounts of bromide ions may interfere with the phase transfer mechanism (due to competition between bromide ion and the reactive anion to be transported by the PTC) so reducing its efficacy.

Where bromide ions are present in catalytic amounts, it has been found that particularly good yields may be obtained using more concentrated solutions of hypochlorite with up to 16% available chlorine.

Although not wishing in any way to be limited by theoretical considerations, it is at present believed that in the process of this invention the phase transfer catalyst and, where present, the bromide ions facilitate the rate-determining step of the reaction in the two-phase system so that the 2-carbamoyl-benzyl alcohol starting material of general formula II is converted to the desired product in preference to competitive oxidative reactions. Upon formation, the carbamic acid internal ester of general formula I is protected from hydrolysis by alkali in the aqueous phase, which would result in the formation of a 2-amino-benzyl alcohol. The product of such hydrolysis would be susceptible to unwanted oxidation in the conditions prevailing in the aqueous medium. Thus the reaction of the present invention has the combined effects of promoting the Hofmann rearrangement and inhibiting undesirable further reactions involving the product, so enabling surprisingly good yields of the carbamic acid internal ester of general formula I to be obtained.

Prior to conversion to the 2-amino-benzyl alcohol of formula III, carbamic acid internal ester of general formula I may be recovered from the reaction mixture in which it is formed. This can, for example, be done by separating off the organic phase and driving off the organic medium, or by chilling the reaction mixture and filtering off the product. However it is often more convenient to drive off the water-immiscible organic solvent from the reaction mixture in which the carbamic acid internal ester is formed, and then without further purification treat the residue containing the ester with a conventional agent which will effect hydrolysis to the 2-amino-benzyl alcohol of formula III, e.g., with an aqueous solution of alkali-metal hydroxide.

When an alkali-metal hydroxide is used to effect the hydrolysis, it is preferably employed in approximately stoichiometric amounts or in slight excess, for example, from 2.1 to 2.5 moles. The alkali-metal hydroxide is most conveniently sodium hydroxide.

The 2-amino-benzyl alcohol of general formula III may be separated from the reaction mixture in which it is formed using well-known techniques such as solvent extraction, or by cooling and filtration. Isopropyl acetate is a convenient solvent to employ in solvent extraction. Purification of the 2-amino-benzyl alcohol of general formula III may be carried out by recrystallization, preferably from toluene, by distillation or by sublimation.

The 2-carbamoyl-benzyl alcohols of general formula II used as starting materials in this invention can be prepared by reacting an appropriately substituted phthalide with ammonia, for example using a lower ($C_1$–$C_5$) alcohol as solvent and a corresponding alkoxide as a catalyst.

The 2-carbamoyl-benzyl alcohols of general formula II can be prepared also by reacting an appropriately substituted phthalide in a suitable solvent such as tetrahydrofuran with liquid ammonia in a reaction tube at elevated temperature for a time sufficient to effect conversion to the 2-carbamoyl-benzyl alcohol, see for example C. J. Belke et al. J. Amer. Chem. Soc. 93, 4552–60 (1971).

The following examples are given, though only by way of illustration, to show some of the preferred reaction conditions and techniques which may be used in accordance with the present invention. In each example, the pH of the aqueous sodium hypochlorite solution was in excess of 11.

EXAMPLE 1:

Preparation of 2-amino-benzyl alcohol.

Stage A: 2-Oxo-dihydrobenzo[d][1,3]oxazine.

10 g of Adogen 464 (a catalyst preparation consisting essentially of methyl trioctyl ammonium chloride, available from Ashland Chemical Company) and 2.7 g (0.023 moles) of potassium bromide were dissolved in 700 ml of isopropyl acetate. 190 g (1.26 moles) of 2-carbamoyl-benzyl alcohol were slurried in the solution formed, and to the slurry was added, over a period of 45 minutes, 670 ml of an aqueous sodium hypochlorite solution (density 1.25 g/l; 15% w/v available chlorine; 1.43 moles NaOCl) in which 12 g (0.3 moles) of sodium hydroxide had previously been dissolved. During the addition of the hypochlorite the reaction mixture was cooled to keep its temperature at 30° C. The reaction was continued for a total time of 2 hours, with stirring, after which time the formation of the desired 2-oxo-dihydrobenzo[d][1,3]oxazine was complete. The 2-oxo-dihydrobenzo[d][1,3]oxazine was not isolated; instead the final reaction mixture was used in Stage B below.

Stage B: 2-Amino-benzyl alcohol.

The reaction mixture from Stage A was boiled so as to drive off the isopropyl acetate solvent. A solution of 100 g of sodium hydroxide in 100 ml of water was added to the residue, and the whole was refluxed for 2 hours. After cooling to 45° C., the product was extracted with four 270 ml portions of isopropyl acetate. The isopropyl acetate was then distilled off and the product recrystallized from toluene to give 100 g (63% of theoretical) of 97-98% pure 2-amino-benzyl alcohol; m.p. 83°-83.5° C.

EXAMPLE 2:

Preparation and isolation of 2-oxo-dihydrobenzo[d][1,3]oxazine.

143 g (0.948 moles) of 2-carbamoyl-benzyl alcohol, 2.3 g (0.0226 moles) of sodium bromide, 6.7 g of Adogen 464 and 806 ml of isopropyl acetate were stirred together in a two liter flask and cooled in a water bath. 504 ml of a 14% w/v solution of sodium hypochlorite (1.0 mole) was added to the stirred mixture over 40 minutes and at 30° C. Vigorous agitation was maintained during the addition and for a further 2 hours. The two-phase reaction mixture was then warmed to 50° C. to dissolve all solids. The organic phase was separated and the medium distilled off. The formed solid was recrystallized from 3 volumes of toluene to form 99 g of the desired product as a pale brown solid; m.p. 112° C.; yield 70%.

A small sample of this product was recrystallized from water, and the recrystallized form had a melting point of 118°-119° C.

The following Examples 3 and 4 illustrate the effect in a particular case of catalyzing the formation of 2-oxo-dihydrobenzo[d][1,3]oxazine with bromide ion.

EXAMPLE 3:

Preparation of 2-amino-benzyl alcohol without bromide ion catalysis.

23.4 g (0.155 moles) of 2-carbamoyl-benzyl alcohol were slurried in 120 ml of isopropyl acetate together with 1 g of Adogen 464. To this was added over 1 hour 0.155 moles of sodium hypochlorite as an aqueous solution containing 15% available chlorine, to which had been added 1.2 g (0.03 moles) of sodium hydroxide. During the addition the temperature was maintained below 30° C. The reaction was continued, with stirring, to complete the formation of 2-oxo-dihydrobenzo[d][1,-3]oxazine.

The organic solvent was then removed by azeotropic distillation, and the residue was hydrolyzed by refluxing with 9 g of sodium hydroxide in 30 ml of water for 3 hours. After cooling, the reaction mixture was extracted with three 75 ml portions of isopropyl acetate and the organic solvent then stripped off to yield crude 2-amino-benzyl alcohol with a yield of 56%.

The crude product was purified by recrystallization from toluene to give a 41% yield of a 98% pure product.

EXAMPLE 4:

Preparation of 2-amino-benzyl alcohol with bromide ion catalysis.

The procedure described in Example 3 was repeated but 0.8 g (0.007 moles) of potassium bromide were dissolved in the slurry of the 2-carbamoyl-benzyl alcohol starting material. An 83% yield of crude 2-amino-benzyl alcohol was obtained. On purification this gave a 63% yield of a product of better than 97% purity.

Thus it can be seen that bromide ion catalysis markedly increased the yield of 2-amino-benzyl alcohol.

EXAMPLE 5:

Preparation of 2-amino-benzyl alcohol.

80 g (assayed 90% = 0.48 moles) of 2-carbamoyl-benzyl alcohol were slurried in 250 ml of isopropyl acetate with 1 g (0.01 moles) of sodium bromide and 2 g (0.009 moles) of benzyl triethylammonium chloride. To this slurry there were charged 296 ml of commercial hypochlorite solution (12.5% w/v available chlorine; 0.52 moles NaOCl) in which 0.7 g (0.018 moles) of sodium hydroxide had previously been dissolved giving a pH of 12. Charging took place over a period of 2½ hours, with vigorous stirring, and cooling to 25° C.

The resultant mixture was warmed to 50° C. and the lower (aqueous) layer discarded. The upper (organic) layer was washed with 50 ml of water which was also discarded. Then 160 ml of water were added to the organic layer and the whole distilled until the head temperature reached 97° C. The resultant solution was cooled to 50° C. and 40 g (1 mole) of sodium hydroxide were added thereto. The resultant mixture was stirred for 30 minutes at 80° C. during which time the desired product separated as an upper layer. The mixture was then cooled to 50° C., the product commencing to crystallize, and extracted three times with isopropyl acetate (2×100 ml, 1×60 ml) and the combined extracts evaporated to dryness. The 43.5 g of crude product thus obtained were recrystallized from toluene (160 ml) to give a yield of 41.7 g (71% on available starting material) of 2-amino-benzyl alcohol; m.p. 82° C.

A similar result can be obtained if there is used in the above example benzyl triethyl ammonium bromide in place of benzyl triethyl ammonium chloride and sodium bromide.

EXAMPLES 6 to 12:

Preparation of 2-oxo-dihydrobenzo[d][1,3]oxazine.

In each of these preparations 80 g (0.48 moles) of 2-carbamoyl-benzyl alcohol and 1 equivalent of aqueous alkaline sodium hypochlorite solution (12% w/v available chlorine) were reacted at 25° C. in 150 ml of isopropyl acetate as the water-immiscible organic medium. Other conditions were as follows:

| | NaOH% w/w in NaOCl solution | KBr | Aliquat 336 | Absolute assayed* Yield | Weight Yield |
|---|---|---|---|---|---|
| 6 | 1.5% | 1 g | 4 g | 71.2% | 104% |
| 7 | 3.3% | 1 g | 4 g | 65.8% | 87% |
| 8 | 5.1% | 1 g | 4 g | 49.8% | 86% |
| 9 | 1.5% | 1 g | 8 g | 73.2% | 109% |
| 10 | 1.5% | 1 g | 2 g | 60.1% | 99% |
| 11 | 1.5% | 2 g | 4 g | 71.6% | 103% |
| 12 | 1.5% | 0.5 g | 4 g | 74.7% | 102% |

*Assay by high pressure liquid chromatography against external standards.

Following the procedure of Example 2 but substituting for 2-carbamoyl-benzyl alcohol appropriately substituted 2-carbamoyl-benzyl alcohols which can be prepared from the corresponding phthalides by the general procedures described hereinabove there can be obtained the 2-oxo-dihydrobenzo[d][1,3]oxazines of formula I having the following substituents:

| | $R^4$ | $R^5$ | $R^6$ | $R^7$ | $R^8$ |
|---|---|---|---|---|---|
| 13 | H | OCH$_3$ | OCH$_3$ | H | H |
| 14 | H | OCH$_3$ | H | OCH$_3$ | H |
| 15 | H | OCH$_3$ | H | H | OCH$_3$ |
| 16 | H | H | H | OCH$_3$ | OC$_2$H$_5$ |
| 17 | H | H | Br | H | H |
| 18 | H | Cl | H | H | H |
| 19 | H | H | H | H | Cl |
| 20 | H | H | H | I | H |
| 21 | H | CH$_3$ | H | H | H |
| 22 | H | H | CH$_3$ | CH$_3$ | H |
| 23 | H | H | (CH$_3$)$_2$CHCH$_3$ | H | H |
| 24 | H | H | Cl | NO$_2$ | H |
| 25 | H | H | NO$_2$ | H | H |
| 26 | CH$_3$ | Cl | H | H | OCH$_3$ |
| 27 | C$_2$H$_5$ | H | H | H | H |
| 28 | n-C$_4$H$_9$ | H | H | H | H |
| 29 | t-C$_4$H$_9$ | H | H | CH$_3$ | H |
| 30 | 4-CH$_3$OC$_6$H$_4$ | H | H | H | H |
| 31 | 4-C$_2$H$_5$OC$_6$H$_4$ | H | H | H | H |
| 32 | 2-ClC$_6$H$_4$ | H | H | H | H |
| 33 | 3-ClC$_6$H$_4$ | H | H | H | H |
| 34 | 3-NO$_2$C$_6$H$_4$ | H | H | H | H |
| 35 | C$_6$H$_5$ | H | H | H | H |
| 36 | 2-CH$_3$C$_6$H$_4$ | H | H | H | CH$_3$ |
| 37 | H | H | H | F | H |
| 38 | n-C$_5$H$_{11}$ | H | H | H | OCH$_3$ |

Following the procedure of Example 1, Stage B, but substituting for the reaction mixture from Stage A the substituted 2-oxo-dihydrobenzo[d][1,3]oxazines Nos. 13 to 38 above, there can be obtained the corresponding substituted 2-amino-benzyl alcohols of formula III.

We claim:

1. A process for preparing a 2-oxo-dihydrobenzo[d][1,3]oxazine of the formula:

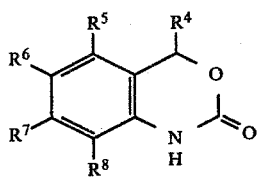

I wherein $R^4$ represents hydrogen or a substituent selected from the group consisting of alkyl of 1 to 6 carbon atoms, phenyl and phenyl substituted by a substituent selected from the group consisting of alkyl of 1 to 4 carbon atoms, alkoxy of 1 to 4 carbon atoms, halo and nitro; $R^5$ and $R^8$, which can be the same or different, each represents hydrogen or a substituent selected from the group consisting of alkyl of 1 to 3 carbon atoms, alkoxy of 1 to 3 carbon atoms and halo; and $R^6$ and $R^7$, which can be the same or different, each represents hydrogen or a substituent selected from the group consisting of alkyl of 1 to 3 carbon atoms, alkoxy of 1 to 3 carbon atoms, halo and nitro; with the proviso that at least two of $R^5$, $R^6$, $R^7$ and $R^8$ are hydrogen, which comprises suspending or dissolving in a substantially water-immiscible organic medium a 2-carbamoyl-benzyl alcohol of the formula:

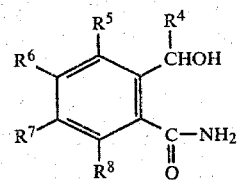

II wherein $R^4$, $R^5$, $R^6$, $R^7$ and $R^8$ are as defined above and treating the formed solution or suspension with an aqueous alkaline solution of a hypochlorite and/or hypobromite having a pH of at least 11 in the presence of a phase transfer catalyst to obtain the compound of formula I.

2. A process according to claim 1 wherein from 0.95 to 1.3 moles of hypochlorite or hypobromite for each mole of the 2-carbamoyl-benzyl alcohol are employed.

3. A process according to claim 2 wherein the hypochlorite or hypobromite and the 2-carbamoyl-benzyl alcohol are employed in substantially equimolar quantities.

4. A process according to claim 1 wherein the organic medium is selected from the group consisting of aromatic hydrocarbon, chlorinated hydrocarbon and carboxylic acid ester.

5. A process according to claim 4 wherein the organic medium is toluene or isopropyl acetate.

6. A process according to claim 1 wherein an alkali metal hypochlorite is employed.

7. A process according to claim 1 wherein the desired pH of the aqueous solution of hypochlorite or hypobromite is obtained by addition thereto of an alkali-metal hydroxide.

8. A process according to claim 7 wherein the alkali-metal hydroxide is added in an amount of about 2% w/w based on the weight of the hypochlorite or hypobromite salt.

9. A process according to claim 1 wherein the phase transfer catalyst is present in an amount from about 0.1 mole % to 5 mole % based on the molar amount of the 2-carbamoyl-benzyl alcohol.

10. A process according to claim 9 wherein the phase transfer catalyst is a quaternary ammonium salt having from 8 to 40 carbon atoms.

11. A process according to claim 10 wherein the quaternary ammonium salt has from 10 to 30 carbon atoms.

12. A process according to claim 11 wherein the quaternary ammonium salt is a bromide or chloride.

13. A process according to claim 1 wherein the phase transfer catalyst is dissolved in the organic medium before the organic medium is contacted with the aqueous alkaline solution of hypochlorite or hypobromite.

14. A process according to claim 1 wherein bromide ions additionally are present.

15. A process according to claim 14 wherein the bromide ions are present in an amount substantially equimolar with the phase transfer catalyst.

16. A process according to claim 1 wherein $R^4$, $R^5$, $R^6$, $R^7$ and $R^8$ each is hydrogen.

17. A process according to claim 16 wherein from 0.95 to 1.3 moles of hypochlorite or hypobromite for each mole of 2-carbamoyl-benzyl alcohol are employed.

18. A process according to claim 17 wherein the hypochlorite or hypobromite and 2-carbamoyl-benzyl alcohol are employed in substantially equimolar amounts.

19. A process according to claim 16 wherein the organic medium is selected from the group consisting of aromatic hydrocarbon, chlorinated hydrocarbon and carboxylic acid ester.

20. A process according to claim 19 wherein the organic medium is toluene or isopropyl acetate.

21. A process according to claim 16 wherein an alkali-metal hypochlorite is employed.

22. A process according to claim 16 wherein the desired pH of the aqueous solution of hypochlorite or hypobromite is obtained by addition thereto of an alkali-metal hydroxide.

23. A process according to claim 22 wherein the alkali-metal hydroxide is added in an amount of about 2% w/w based on the weight of the hypochlorite or hypobromite salt.

24. A process according to claim 16 wherein the phase transfer catalyst is present in an amount from about 0.1 mole % to 5 mole % based on the molar amount of 2-carbamoyl-benzyl alcohol.

25. A process according to claim 24 wherein the phase transfer catalyst is a quaternary ammonium salt having from 8 to 40 carbon atoms.

26. A process according to claim 25 wherein the quaternary ammonium salt has from 10 to 30 carbon atoms.

27. A process according to claim 26 wherein the quaternary ammonium salt is a bromide or chloride.

28. A process according to claim 16 wherein the phase transfer catalyst is dissolved in the organic medium before the organic medium is contacted with the aqueous alkaline solution of hypochlorite or hypobromite.

29. A process according to claim 16 wherein bromide ions additionally are present.

30. A process according to claim 29 wherein the bromide ions are present in an amount substantially equimolar with the phase transfer catalyst.

31. A process according to claim 16 wherein the pH of the aqueous alkaline solution of hypochlorite or hypobromite is at least 11.5.

* * * * *